United States Patent [19]

Dalcanale

[11] Patent Number: 4,673,759
[45] Date of Patent: Jun. 16, 1987

[54] PROCESS FOR THE PREPARATION OF 2-ALKYL CYCLOPENT-2-ENONES

[75] Inventor: Enrico Dalcanale, Novara, Italy

[73] Assignee: Montedison S.p.A., Milan, Italy

[21] Appl. No.: 835,246

[22] Filed: Mar. 3, 1986

[30] Foreign Application Priority Data

Mar. 5, 1985 [IT]  Italy ................................ 19770 A/85

[51] Int. Cl.$^4$ ........................................... C07C 67/30
[52] U.S. Cl. ................................... 560/122; 568/341; 568/346; 564/454; 564/455; 558/432; 549/322; 549/323; 549/326; 549/524
[58] Field of Search ............... 549/322, 323, 326, 524, 549/526; 568/341, 346; 558/432; 564/454, 455; 560/122

[56] References Cited

U.S. PATENT DOCUMENTS

| | | | |
|---|---|---|---|
| 3,299,100 | 1/1967 | Phillips | 549/322 |
| 3,755,370 | 8/1973 | Fauran et al. | 549/323 |
| 4,138,584 | 2/1979 | Klemmensen et al. | 549/326 |
| 4,229,353 | 10/1980 | Klemmensen et al. | 549/322 |

OTHER PUBLICATIONS

Eaton et al., J. Org. Chem., vol. 38, pp. 4071–4073 (1973).
DePuy et al., J. Org. Chem., vol. 29, p. 2810 (1964).
Venturello et al., J. Org. Chem., vol. 48, pp. 3831–3833 (1983).
Fieser et al., "Reagents for Organic Synthesis", pp. 135–137 (1967).

*Primary Examiner*—James H. Reamer
*Attorney, Agent, or Firm*—Stevens, Davis, Miller & Mosher

[57] ABSTRACT

A process for the preparation of 2-alkyl cyclopent-2-enones having the formula:

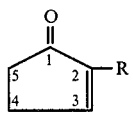

wherein R is as defined hereinafter. An α-olefin having the formula $CH_2=CH-CH_2R$ is oxidized to the corresponding epoxide. The epoxide is reacted with an alkylating agent having the formula $Na^+[CH(COOR'')_2]^-$, wherein R'' is an ethyl, an isopropyl, or an isobutyl radical. An α-carbalkoxy-γ-alkyl lactone is obtained, which, through saponification and decarboxylation, yields a γ-alkyl lactone having the formula:

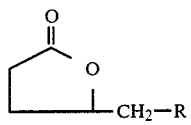

which is reacted with a protic acid, thereby obtaining, by cyclization, the desired 2-alkylcyclopent-2-enone. The obtained products are intermediates for the production of pharmaceutical products and of drugs for veterinary use, in particular prostaglandin.

9 Claims, No Drawings

PROCESS FOR THE PREPARATION OF 2-ALKYL CYCLOPENT-2-ENONES

The present invention relates to a process for preparing 2-alkylcyclopent-2-enones having the formula:

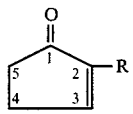 (I)

wherein R represents one of the following groups:
$C_nH_{2n+1}$ (the chain being linear or branched);
$(CH_2)_n$-COOR';
$(CH_2)_n$-NR'$_2$;
$(CH_2)_n$-OR';
$(CH_2)_n$X, wherein X=Cl, Br, I or F; or
$(CH_2)_n$-CN.

In each of these groups, n ranges from 1 to 20 and R' is an alkyl radical containing up to 5 carbon atoms, a benzyl radical or a phenyl radical, these last two radicals optionally carrying, in the aromatic nucleus, one or more substituent groups (inert under the reaction conditions).

Cyclopentenones (I) are useful intermediates for the manufacture of pharmaceutical products and of drugs for veterinary use, in particular, prostaglandins.

According to a known process, an olefin is reacted, in a first step, with trihydrated manganese acetate, potassium permanganate, acetic anhydride and anhydrous sodium acetate, all in a large excess with respect to the olefin, thereby obtaining a γ-alkyl lactone, which, in a second step, is cyclized by means of polyphosphoric acid, thereby obtaining the final product. Such a process gives rise to low yields and requires particular reactants which are expensive and can be handled only with difficulty; furthermore, the reactions lead to complex mixtures of products from which the γ-alkyl lactone and the final product may be separated only with difficulty.

An object of the invention is to provide a process for the preparation of 2-alkylcyclopent-2-enones having formula (I) with rather good yields, and a second object is to provide a process starting from raw materials which are cheap and can be handled easily. A third object is to provide a process allowing the intermediate products and the final product to be separated easily.

These and still other objects are easily achieved by means of a process characterized by the following steps:

(a) an α-olefin having the formula $$CH_2=CH-CH_2-R \qquad (II)$$

is oxidized to the epoxide

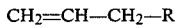 (III)

(b) epoxide (III) is reacted, under reflux conditions, with an alkylating agent having the formula:

(where R" is an ethyl, an isopropyl, or an isobutyl radical) in the presence of a malonic ester having the formula:

$$COOR''-CH_2-COOR''$$

in an alcoholic solvent having the formula R"OH. The alkylating agent is used in a practically equimolar ratio with respect to the epoxide, and said malonic ester is used in a molar ratio with respect to the epoxide of from 0.5 to 2. An α-carbalkoxy-γ-alkyl lactone is thus obtained, having the formula:

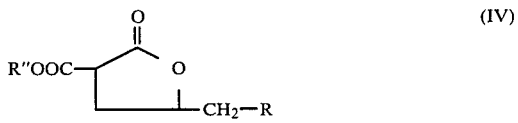 (IV)

(c) said lactone (IV) is saponified in an alkaline medium, thereby obtaining the corresponding acid;

(d) the acid is decarboxylated, at temperatures from 100° to 160° C., thereby obtaining a γ-alkyl lactone having the formula (V):

 (V)

(e) said lactone (V) is reacted at 20° to 100° C. with a protic acid, thereby obtaining, by cyclization, the desired 2-alkylcyclopent-2-enone having the formula (I).

In the starting olefin (and consequently in 2-allyl cyclopent-2-enone (I) as well), n ranges preferably from 1 to 10. The preferred substituent groups are $C_nH_{2n+1}$ or $(CH_2)_n$-COOR'. When radical R' is a benzyl or a phenyl radical, these groups may be substituted in the aromatic nucleus by one or more inert groups (usually from 0 to 2), selected generally from the class consisting of NR$_2$''', OR''', X, CN and NO$_2$, where X has the meaning given above and where R''' is an alkyl radical containing up to 5 carbon atoms, a benzyl radical or a phenyl radical.

The oxidation of the olefin $CH_2=CH-CH_2-R$ to the epoxide

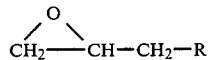

may be carried out by means of well-known methods, according to which the substituents, optionally present in group R, remain unaltered. A suitable method resides in oxidizing the olefin by means of m-chloroperbenzoic acid; such method providing the epoxide with yields over 90% and allowing of a very simple working.

Another suitable method resides in oxidizing the olefin with $H_2O_2$ in the presence of a catalyst based on tungstate and phosphate ions; such a method is described, for instance, in an article by C. Venturello et al, on the *J. Org. Chem.*, 48, 13831, 1983. This last method is more economical than the first one, giving rise to good epoxide yields (about 70%), and allowing one to recover much of the non-reacted olefin. It is clear that still other methods may be used, provided that they do not alter the substituents optionally present in group R.

The second step resides in alkylating epoxide (III) by means of an alkylating agent $Na^+[CH(COOR'')_2]^-$, wherein R'' is an ethyl, an isopropyl, or an isobutyl radical; the reaction is described, for instance, in an article by C. H. Depuy et al, in the *J. Org. Chem.*, 1964, page 2810, the reaction scheme being:

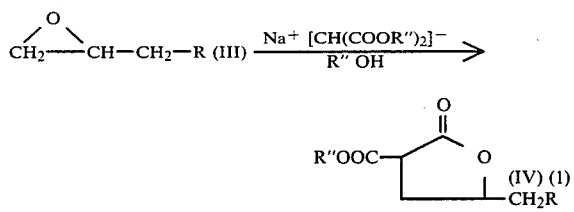

The epoxide is reacted with the above-mentioned alkylating agent in the presence of a malonic ester having the formula

COOR''—CH$_2$—COOR''.

The alkylating agent should be used in a substantially equimolar ratio with respect to the epoxide, and said malonic ester should be used in a molar ratio with respect to the epoxide of from 0.5 to 2; preferably, such molar ratio should be about 1. The reaction must be carried out under reflux conditions. The alkylation of epoxide (III) turned out to be completely regioselective, providing only the attack product in the non-substituted position.

An intramolecular cyclization, yielding lactone (IV), follows the alkylation. The reaction can be carried out suitably as follows: metal sodium, in a finely subdivided form, is added to anhydrous alcohol R''OH. When the sodium is wholly dissolved, malonic ester COOR'—CH$_2$—COOR'' is added in such an amount as to have in solution both the alkylating agent and the non-reacted malonic ester, according to the molar ratios defined hereinbefore. Alkylating agent $Na^+[CH(COOR'')_2]^-$ forms immediately. At this point, the solution is subjected to reflux conditions and the epoxide is added gradually; the whole is made to react for a time ranging from 1 to about 8 hours, depending on the nature of substituent R.

α-carboxy-γ-alkyl lactone (IV) is then saponified in an alkaline medium, thereby obtaining the corresponding acid (VI):

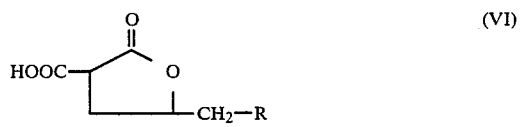

This reaction may be carried out as follows: an aqueous solution of sodium carbonate is added to the reaction mixture of the preceding step and the two phases are mixed generally at from 50° C. to the reflux temperature. Acid (VI) may be separated from the reaction mixture as follows: alcohol R''OH is distilled, while leaving the acid in the aqueous phase and separating said acid successively by crystallization or by extraction by means of an organic solvent.

Acid (VI) is then decarboxylated, at 100° to 160° C., thereby obtaining a γ-alkyl lactone having the formula:

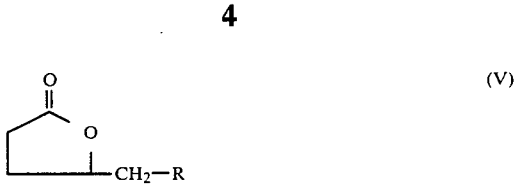

The decarboxylation should be carried out preferably at 120° to 140° C. Some of the γ-alkyl lactones may be used for perfumes or essential oils.

γ-alkyl lactone (V) is then reacted at 20° to 100° C. (preferably 50° to 60° C.), with a protic acid, thereby obtaining, by cyclization, the desired 2-alkyl-cyclopent-2-enone having the formula (I).

The protic acids are generally selected from the group consisting of polyphosphoric acid, 96% sulphuric acid (weight/volume), and a mixture consisting of $CH_3$—$SO_3H$ and $P_2O_5$. The mixture consisting of $CH_3$—$SO_3H$ and $P_2O_5$ turned out to be particularly suitable. In such a mixture, the $CH_3$—$SO_3H/P_2O_5$ weight ratio usually ranged from 10 to 20, and is preferably equal to about 10. The preparation of the mixture consisting of $CH_3$—$SO_3H$ and $P_2O_5$ is described, for instance, in an article by P. E. Eaton et al, *J. Org. Chem.*, 38, 4071, 1973, and the cyclization reaction by means of a protic acid is described, for instance in an article by E. Uhlig et al, *Adv. Org. Chem.*, 1, 35, 1960.

The reaction may be carried out as follows: γ-alkyl lactone (V) is added to the protic acid, at room temperature. The resultant solution is heated, as described above, for a time generally ranging between 5 and 24 hours, depending on the nature of substituent R. Then, the solution is poured into water and the resultant solution is extracted by means of an organic solvent immiscible with water. The organic phase is separated, dehydrated and concentrated in order to yield an oil. The product is then isolated by distillation under reduced pressure, by crystallization or by separation on a chromatographic column, or by the combined use of two of these techniques.

The main advantages of the process of the present invention may be summarized as follows:
the operative conditions are very simple;
the starting substrata and the reactants are cheap;
the first four steps give rise to a high yield; therefore, the global or overall yield of the process is good; and
the intermediate products and the final product may be easily separated.

The following examples will still better illustrate the invention, but without limiting the scope thereof.

EXAMPLE 1

Epoxidation by Means of Metachloro-Perbenzoic Acid 53.08 g (0.25 moles) of ethyl 10-undecenoate were introduced into a 1000 cm$^3$ flask provided with stirrer, reflux cooler, thermometer, and dropping funnel. Then, 60.92 g (0.3 moles) of meta-chloroperbenzoic acid (85% concentration), dissolved in 650 cm$^3$ of chloroform, were added drop-by-drop over 2 hours. Once the addition was over, the mixture was kept under reflux conditions for 2 hours, and then the solution was cooled and shaken with a 10% b.w. aqueous solution of sodium bicarbonate. The organic phase was washed with water until neutral, dehydrated over anhydrous sodium sulphate ($Na_2SO_4$), and dried.

The thus-obtained oil was distilled under reduced pressure (108° to 110° C./2.10$^{-1}$ mm Hg), thereby providing 52.5 g (0.23 moles) of ethyl 10,11-epoxydecanoate, with a yield of 92%.

EXAMPLE 2

Epoxidation with Hydrogen Peroxide 0.360 g ($1.08.10^{-3}$ moles) of sodium tungstate ($Na_2WO_4.2H_2O$) dissolved in 6 cm$^3$ of water, 0.55 cm$^3$ ($2.24.10^{-3}$ moles) of 40% phosphoric acid (weight/volume), and 20.5 cm$^3$ ($2.11.10^{-3}$ moles) of 35% hydrogen peroxide (weight/volume) were added, following this order, to a 250 cm$^3$ flask equipped with mechanical stirrer, reflux cooler, and thermometer. The pH was brought to 1.6 by means of an aqueous solution of 30% sulphuric acid at (weight/volume). At this point, 53.08 g ($2.5.10^{-1}$ moles) of ethyl 10-undecenoate in 10 cc of 1-2-dichloroethane and 0.179 g ($4.48.10^{-4}$ moles) of tricaprylmethylammonium chloride were added. The resultant two-phase mixture was heated with vigorous stirring at 70° C. for 4 hours, until the whole amount of hydrogen peroxide was consumed, after which the mixture was treated with a saturated aqueous solution of $Na_2SO_3$ (in order to eliminate possible traces of $H_2O_2$) and $NaHCO_3$. The organic phase was separated, dehydrated over anhydrous sodium sulphate, concentrated and distilled under reduced pressure.

Two fractions were obtained:

at 96° to 98° C./$2.10^{-1}$ mm Hg: 9.15 g ($4.31.10^{-2}$ moles) of ethyl 10-undecenoate;

at 108° to 110° C./$2.10^{-1}$ mm Hg: 39.4 g ($1.73.10^{-1}$ moles) of ethyl 10,11-epoxyundecanoate. Yield: 69%. Selectivity: 83%.

EXAMPLE 3

Alkylation, Saponification, and Decarboxylation 100 cm$^3$ of anhydrous ethyl alcohol and 1.01 g ($4.38.10^{-2}$ moles) of finely subdivided sodium were added, in this order, to a 500 cm$^3$ flask provided with magnetic stirrer, reflux cooler, thermometer, and dropping funnel. The mixture was kept at room temperature until the whole amount of sodium was dissolved, after which 14.03 g ($8.76.10^{-2}$ moles) of diethylmalonate were added. The whole was kept under reflux conditions and 10.0 g ($4.32.10^{-2}$ moles) of ethyl 10,11-epoxyundecanoate were added, drop-by-drop, over 1 hour. Once the addition was over, the mixture was kept under stirring for about 3 hours. Then, 3.00 g of sodium carbonate in 100 cm$^3$ of water were added and the alcohol was azeotropically distilled. The residual aqueous solution was acidified by means of an aqueous solution of 10% hydrochloric acid (weight/volume) and cooled down.

The precipitation overnight of 12 g of a crystalline white solid was noted, which was separated and decarboxylated in a stream of nitrogen at 140° C., thereby providing 9.66 g ($3.98.10^{-2}$ moles) of 13-carboxy-$\gamma$-tridecalactone in the form of a pure white oil, with a yield of 91%.

EXAMPLE 4

Cyclization 27 cm$^3$ (36 g) of distilled methanesulfonic acid and 4 g of phosphoric anhydride were added, in this order, to a 100 cm$^3$ flask provided with magnetic stirrer and thermometer, pressurized with nitrogen. The whole was kept under stirring for 1 hour at room temperature until a limpid solution was obtained. Then, 1.0 g ($4.13.10^{-3}$ moles) of 13-carboxy-$\gamma$-tridecalactone were added, the temperature was raised up to 60° C., and the whole was made to react for 16 hours. Then, the solution was dripped into 100 cm$^3$ of water and the resultant mixture was kept under stirring for about 10 minutes. After many extractions with chloroform (4×30 cm$^3$), the organic phase was separated, washed with an aqueous solution of sodium bicarbonate until neutral, dehydrated over anhydrous sodium sulphate and dried, thereby obtaining 0.97 g of a red oil.

This oil was treated with diazomethane ($CH_2N_2$) in order to form the methyl ester of the desired product. The resultant oil was conveyed onto a silica gel column, using hexane-ether as eluent in a 1:1 ratio by volume. Two fractions were recovered:

0.094 g ($4.2.10^{-4}$ moles) of 2-(6'-carbomethoxy-hexyl)cyclohex-2-ene-1-one;

0.380 g ($1.69.10^{-3}$ moles) of 2-(7'-carbomethoxy-heptyl)cyclopent-2-ene-1-one.

The yield of the latter was 41%. The molar ratio between the cyclohexenone and the cyclopentenone was 4:1.

EXAMPLES 5-8

Following the operating conditions of Examples 1-4, but for the esterification by means of diazomethane,

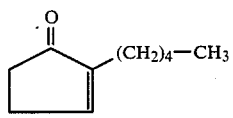

was prepared, starting from $CH_2\!=\!CH\!-\!(CH_2)_5\!-\!CH_3$.

The scheme of the reactions and the yields were as follows:

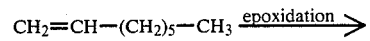

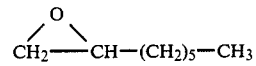

with meta-chloroperbenzoic acid: Yield 92%; with $H_2O_2$: Yield 50%, selectivity 95%; alkylation, saponification,

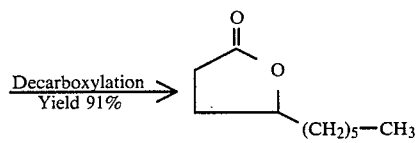

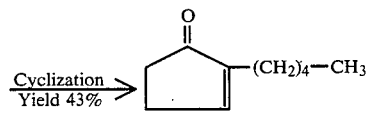

EXAMPLES 9-12

Following the operating conditions of Examples 1-4, but for esterification by means of diazomethane,

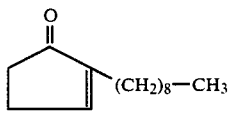

was prepared, starting from $CH_2=CH-(CH_2)_9-CH_3$.

The scheme of the reactions and the yields were as follows:

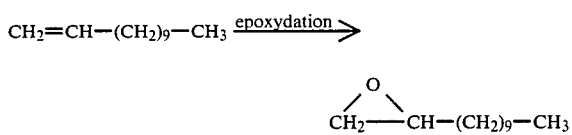

with metachloroperbenzoic acid: Yield 91%; with $H_2O_2$: Yield 50%, Selectivity 95%; alkylation, saponification,

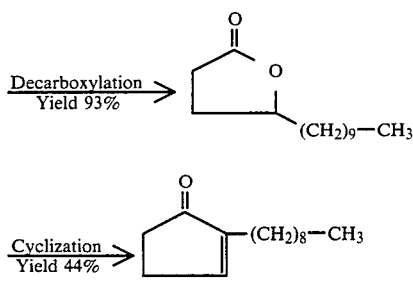

EXAMPLES 13-16

Following the operative conditions of Examples 1-4:

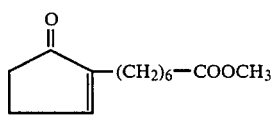

was prepared, starting from $CH_2=CH-(CH_2)_7-COOC_2H_5$.

The scheme of the reactions and the yields were as follows:

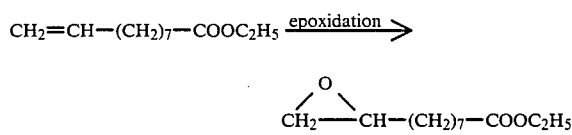

with meta-chloroperbenzoic acid: Yield 92% with $H_2O_2$: Yield 70% and Selectivity 85% alkylation, saponification,

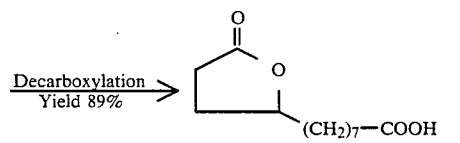

What is claimed is:

1. A process for the preparation of a 2-alkylcyclopenten-2-one having formula:

where R is $C_nH_{2n+1}$ (linear or branched); $(CH_2)_n-COOR'$; $(CH_2)_n-NR'_2$; $(CH_2)_n-OR'$; $(CH_2)_nX$ or $(CH_2)_n-CN$, n ranges from 1 to 20, X is Cl, Br, I or F, and R' is an alkyl group containing up to 5 carbon atoms, a benzyl group, or a phenyl group, the last two groups having optionally one or more substituent groups on the ring, wherein a saturated gamma-alkyl-lactone:

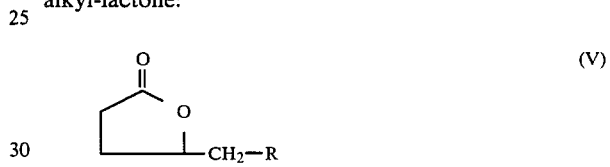

is reacted at 20°-100° C. with a protic acid, thereby obtaining, by rearrangement, a 2-alkyl-cyclopenten-2-one (I), characterized in that said gamma-alkyl-lactone (V) is obtained through the following steps:

(a) an epoxide:

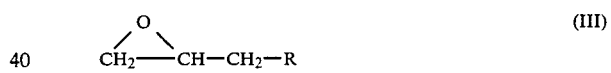

is made to react with an alkylating agent having the formula $Na^+[CH(COOR'')_2]^-$ (R'' being an ethyl, isopropyl or isobutyl radical), in the presence of the malonic ester $COOR''-CH_2-COOR''$ and of an alcoholic solvent R''OH, the alkylating agent being in substantially equimolar ratio with respect to said epoxide and the malonic ester being in a molar ratio, with respect to said epoxide, of from 0.5 to 2, an alpha-carbalkoxy-gamma-alkyl-lactone being thus obtained having the formula:

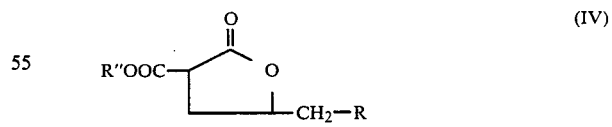

(b) said carbalkoxy-alkyl-lactone (IV) is saponified in an alkaline medium, thereby obtaining the corresponding acid, and such acid is decarboxylated, at 100°-160° C., thereby obtaining a gamma-alkyl-lactone having formula (V).

2. A process according to claim 1, wherein n ranges from 1 to 10.

3. A process according to claim 1 or 2, wherein R is selected from the class consisting of $C_nH_{2n+1}$ and $(CH_2)_n-COOR'$.

4. A process according to claim 1 or 2, wherein, in the second step (b), the malonic ester is used in a molar ratio, with respect to the epoxide, of about 1.

5. A process according to claim 1 or 2, wherein, in the fourth step (d), the acid is decarboxylated at 120° to 140° C.

6. A process according to claim 1 or 2, wherein the fifth step (e) is carried out at 50° to 60° C.

7. A process according to claim 1 or 2, wherein, in the fifth step (e), the protic acid is selected from the class consisting of a mixture of $CH_3$—$SO_3H$ and $P_2O_5$, polyphosphoric acid, and sulphuric acid.

8. A process according to claim 7, wherein the protic acid is a mixture consisting of $CH_3$-$SO_3H$ and $P_2O_5$, in a weight ratio from 10 to 20.

9. A process according to claim 8, wherein said ratio is about 10.

* * * * *